(12) United States Patent
Greep

(10) Patent No.: US 8,211,103 B2
(45) Date of Patent: Jul. 3, 2012

(54) ELECTROSURGICAL INSTRUMENT WITH ADJUSTABLE POWER CABLE

(75) Inventor: Darcy W. Greep, South Jordan, UT (US)

(73) Assignee: Megadyne Medical Products, Inc., Draper, UT (US)

( * ) Notice: Subject to any disclaimer, the term of this patent is extended or adjusted under 35 U.S.C. 154(b) by 659 days.

(21) Appl. No.: 12/429,867

(22) Filed: Apr. 24, 2009

(65) Prior Publication Data

US 2010/0274242 A1    Oct. 28, 2010

(51) Int. Cl.
*A61B 18/18*    (2006.01)

(52) U.S. Cl. ......................................... 606/42

(58) Field of Classification Search ..................... 606/41, 606/42

See application file for complete search history.

(56) References Cited

U.S. PATENT DOCUMENTS

| | | | |
|---|---|---|---|
| 4,112,950 A | 9/1978 | Pike | |
| 4,545,375 A | 10/1985 | Cline | |
| 4,562,838 A | 1/1986 | Walker | |
| 4,688,569 A | 8/1987 | Rabinowitz | |
| 4,911,159 A * | 3/1990 | Johnson et al. | 606/37 |
| 5,055,100 A | 10/1991 | Olsen | |
| 5,085,657 A | 2/1992 | Ben-Simhon | |
| 5,195,959 A | 3/1993 | Smith | |
| 5,217,457 A | 6/1993 | Delahuerga et al. | |
| 5,226,904 A | 7/1993 | Gentelia et al. | |
| 5,234,428 A | 8/1993 | Kaufman | |
| 5,364,395 A * | 11/1994 | West, Jr. | 606/46 |
| 5,376,089 A | 12/1994 | Smith | |
| 5,395,312 A | 3/1995 | Desai | |
| 5,413,575 A | 5/1995 | Haenggi | |
| 5,431,650 A | 7/1995 | Cosmescu | |
| 5,514,089 A | 5/1996 | Walbrink et al. | |
| D370,731 S | 6/1996 | Corace et al. | |
| 5,609,573 A | 3/1997 | Sandock | |
| 5,658,249 A * | 8/1997 | Beland et al. | 604/33 |
| 5,693,044 A | 12/1997 | Cosmescu | |
| 5,800,431 A | 9/1998 | Brown | |
| 5,836,909 A | 11/1998 | Cosmescu | |
| 5,836,944 A | 11/1998 | Cosmescu | |
| 5,928,137 A * | 7/1999 | Green | 600/160 |
| 5,951,548 A | 9/1999 | DeSisto et al. | |
| 6,099,525 A | 8/2000 | Cosmescu | |
| 6,117,134 A | 9/2000 | Cunningham et al. | |
| 6,142,995 A | 11/2000 | Cosmescu | |
| 6,146,353 A | 11/2000 | Platt, Jr. | |
| 6,149,648 A | 11/2000 | Cosmescu | |
| 6,258,088 B1 | 7/2001 | Tzonev et al. | |
| 6,524,307 B1 | 2/2003 | Palmerton et al. | |
| 6,558,379 B1 | 5/2003 | Batchelor et al. | |

(Continued)

*Primary Examiner* — Kevin C Sirmons
*Assistant Examiner* — Andrew Gilbert
(74) *Attorney, Agent, or Firm* — Workman Nydegger (57) ABSTRACT

An electrosurgical instrument that reduces the amount of fatigue experienced by a physician performing electrosurgery includes a hand piece that is connected to an electrosurgical generator by way of an electrical cable. The electrical cable is connected to the hand piece at a central portion of the hand piece, which reduces the resistance to the movement of the electrosurgical instrument created by the weight of the electrical cable. The reduced resistance leads to less fatigue in a physician's hand during electrosurgery. The hand piece can include a channel system that receives a portion of the electrical cable therein and allows a physician to adjust the location on the hand piece at which the electrical cable exits the hand piece. The channel system can include one or more side channels and/or longitudinal channels. The channels can include detents that define multiple exit locations from the channel system for the electrical cable.

20 Claims, 5 Drawing Sheets

U.S. PATENT DOCUMENTS

| | | |
|---|---|---|
| 6,616,658 B2 | 9/2003 | Ineson |
| D493,530 S * | 7/2004 | Reschke ..................... D24/144 |
| 6,896,672 B1 | 5/2005 | Eggers et al. |
| 6,974,458 B2 * | 12/2005 | Muller et al. ................... 606/46 |
| D521,641 S | 5/2006 | Reschke et al. |
| 7,141,049 B2 | 11/2006 | Stern et al. |
| 7,156,842 B2 | 1/2007 | Sartor et al. |
| 7,156,844 B2 | 1/2007 | Reschke et al. |
| 7,241,294 B2 | 7/2007 | Reschke |
| 7,244,257 B2 | 7/2007 | Podhajsky et al. |
| 7,393,354 B2 | 7/2008 | Buchman, II et al. |

* cited by examiner

ELECTROSURGICAL INSTRUMENT WITH ADJUSTABLE POWER CABLE

BACKGROUND OF THE INVENTION

1. Technical Field

This invention relates to the field of electrosurgery. More particularly, the invention relates to electrosurgical instruments that facilitate the performance of electrosurgery while reducing the amount of fatigue experienced by a physician performing an electrosurgical procedure.

2. The Relevant Technology

As is known to those skilled in the art, modern surgical techniques typically employ radio frequency (RF) power to cut tissue and coagulate bleeding encountered in performing surgical procedures. For a historical perspective and details of such techniques, reference is made to U.S. Pat. No. 4,936, 842, issued to D'Amelio et al., and entitled "Electroprobe Apparatus," the disclosure of which is incorporated by this reference.

As is known to those skilled in the medical arts, electrosurgery is widely used and offers many advantages including the use of a single surgical instrument for both cutting and coagulation. A monopolar electrosurgical generator system has an active electrode, such as in the form of an electrosurgical instrument having a hand piece and a conductive electrode or tip, which is applied by the surgeon to the patient at the surgical site to perform surgery and a return electrode to connect the patient back to the generator.

The electrode or tip of the electrosurgical instrument is small at the point of contact with the patient to produce an RF current with a high current density in order to produce a surgical effect of cutting or coagulating tissue. The return electrode carries the same RF current provided to the electrode or tip of the electrosurgical instrument, thus providing a path back to the electrosurgical generator.

To make the electrical connection for the RF current between the electrosurgical generator and the electrosurgical instrument, a cable having an electrically conductive core extends from the electrosurgical generator to the electrosurgical instrument. The cable may also include a cord with additional conductors. The cord provides a connection for transmitting control signals from the electrosurgical instrument to the electrosurgical generator. The control signals may be used to cause the generator to deliver RF currents for different cutting modes such as cut, coagulate, and cut-coagulate blend.

The cable has certain flexibility and weight characteristics that limit the ability of the physician during a surgical procedure. For example, the weight/moment-arm effect, and drag of the cable electrically linking the generator and the electrosurgical instrument and the connection location of the cable and the electrosurgical instrument limit the physician's ability to continually hold and use the electrosurgical instrument. The electrode or tip is received within one end of the hand piece (commonly referred to as a pencil) and the cable typically enters into the opposite end of the hand piece. As the physician manipulates the electrosurgical instrument during a surgical procedure, the weight of the cable continually pulls the end of the electrosurgical instrument to which it is attached. More specifically, as the physician moves his or her wrist or adjusts the orientation of the electrosurgical instrument with his or her fingers so as to bring the electrode into contact with the patient's tissue, the weight of the cable resists the physician's movement. The constant resistance or drag created by the cable can cause the physician to become fatigued during a surgical procedure that requires extensive and continual use of the electrosurgical instrument.

Additionally, many electrosurgical procedures are performed on very sensitive parts of the body, such as on or around the eyes. When performing such procedures, the physician must control the movements of the electrode with great precision and accuracy. The resistance or drag created by the cable can make it more difficult for the physician to be as precise and accurate. For instance, when moving the electrosurgical instrument to make a delicate incision, the physician must accurately compensate for the cable resistance. If the physician overcompensates, an incision that is too deep or too long can result. Alternatively, if the physician undercompensates, multiple passes may be required to achieve the desired incision. Furthermore, the fatigue caused by the cable resistance can adversely affect the physician's ability to accurately compensate for the cable resistance.

The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY

Generally, the present invention relates to an electrosurgical instrument that facilitates the performance of electrosurgery while reducing the amount of fatigue experienced by a physician performing the electrosurgery. The electrosurgical instrument includes a hand piece that holds an electrode tip in one end thereof. The hand piece is connected to an electrosurgical generator by way of an electrical cable. In contrast to most electrosurgical instruments that have an electrical cable connected to an end of the hand piece, the electrosurgical instrument of the present invention provides for the electrical cable to be connected to the hand piece at a central portion of the hand piece. The central connection location of the electrical cable to the hand piece reduces the resistance to the movement of the electrosurgical instrument created by the weight of the electrical cable. The reduced resistance leads to less fatigue in the physician's hand during electrosurgery. In addition to the central connection location between the hand piece and the electrical cable, the hand piece can be configured to allow the physician to adjust the location on the hand piece at which the electrical cable exits the hand piece. The physician can, therefore, adjust the electrical cable relative to the hand piece in order to customize the electrosurgical instrument to the physician's liking.

According to one aspect of one exemplary configuration of the present invention, the electrosurgical instrument includes an electrical cable that can be coupled to an electrosurgical generator to transmit the electrical energy from the electrosurgical generator to the hand piece of the electrosurgical instrument. The hand piece has a proximal end, a distal end, and a central portion disposed therebetween. A conductive electrode tip can be received within the distal end of the hand piece for transmitting the electrical energy from the hand piece to the tissue of a patient. The central portion of the hand piece has a receptacle configured to receive therein an end of the electrical cable. In addition, the hand piece further includes a channel system that enables a user of the electrosurgical instrument to selectively position at least a portion of the electrical cable within the channel system to thereby select an exit location from the channel system for the electrical cable.

In one exemplary embodiment, the channel system includes first and second opposing side channels and a longitudinal channel. The first and second opposing side channels extend from the receptacle to opposing sides of the hand piece. The first and second opposing side channels are configured to selectively and removably receive at least a portion of the electrical cable therein such that the electrical cable may exit the channel system from the central portion and on either side of the hand piece. The longitudinal channel extends from the receptacle toward the proximal end of the hand piece. The longitudinal channel comprises a plurality of detents spaced along a length of the longitudinal channel and which are configured to selectively and removably receive at least a portion of the electrical cable therebetween. The plurality of detents defines a plurality of discrete exit locations from which the electrical cable can exit the channel system. The user of the electrosurgical instrument can selectively position the electrical cable within the longitudinal channel or the side channels to select the exit location of the electrical cable from the channel system.

According to other exemplary embodiments of the present invention, the channel system formed in the hand piece can include fewer or more channels. The channel system can be formed with a one or more side channels, one or more longitudinal channels, or a combination thereof Additionally, the channel system can be formed with one or more channels that can be employed with an evacuation hose that is associated with the electrosurgical instrument. The evacuation hose channels can be configured to selectively receive and retain a portion of the evacuation hose such that a user of the electrosurgical instrument can selectively adjust the exit location of the evacuation hose from the channel system.

This Brief Summary is provided to introduce a selection of concepts in a simplified form that are further described below in the Detailed Description. This Brief Summary is not intended to identify key features or essential features of the claimed subject matter, nor is it intended to be used as an aid in determining the scope of the claimed subject matter.

Additional features and advantages will be set forth in the description which follows, and in part will be obvious from the description, or may be learned by the practice of the teachings herein. Features and advantages of the invention may be realized and obtained by means of the instruments and combinations particularly pointed out in the appended claims. Features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION

The present invention relates to an electrosurgical instrument that facilitates the performance of electrosurgery while reducing the amount of fatigue experienced by a physician performing the electrosurgery. The electrosurgical instrument includes a hand piece that holds an electrode tip in one end thereof The hand piece is connected to an electrosurgical generator by way of an electrical cable. In contrast to most electrosurgical instruments that have an electrical cable connected to an end of the hand piece, the electrosurgical instrument of the present invention provides for the electrical cable to be connected to the hand piece at a central portion of the hand piece. The central connection location of the electrical cable to the hand piece reduces the resistance to the movement of the electrosurgical instrument created by the weight/moment-arm effect, and drag of the electrical cable. The reduced resistance leads to less fatigue in the physician's hand and arm during electrosurgery. In addition to the central connection location between the hand piece and the electrical cable, the hand piece can be configured to allow the physician to adjust the location on the hand piece at which the electrical cable exits the hand piece. The physician can, therefore, selectively adjust the electrical cable relative to the hand piece in order to customize the electrosurgical instrument to the physician's liking.

Figure 1:
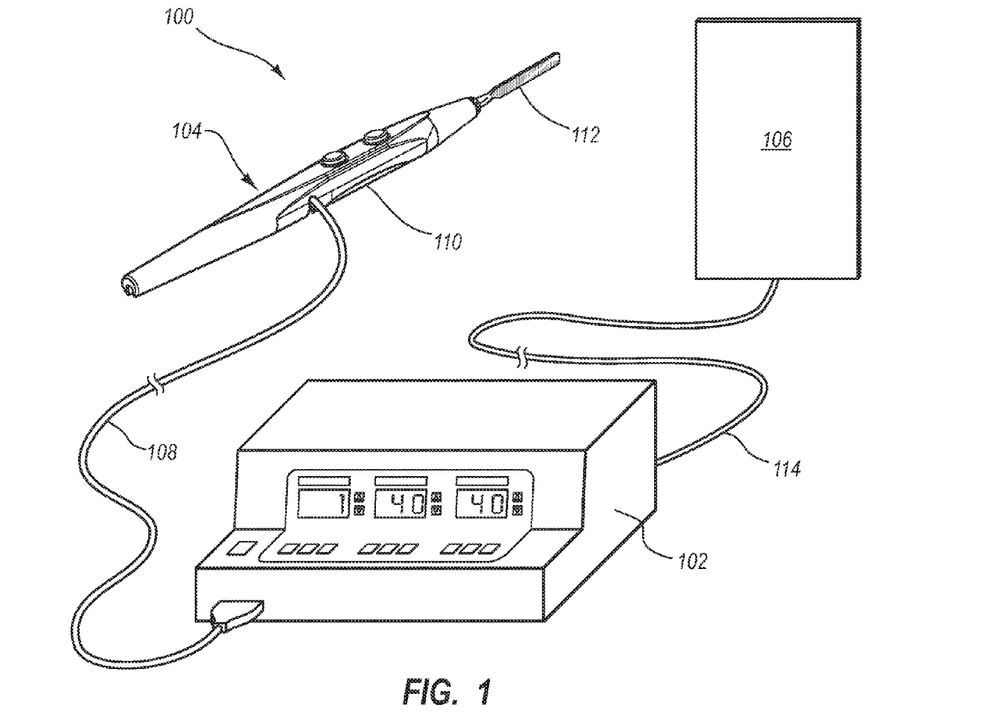
FIG. 1 illustrates an electrosurgical system with an electrosurgical instrument according to one exemplary embodiment of the present invention.

Referring to FIG. 1, an exemplary environment is illustrated that provides one operating environment for use of the present invention. In FIG. 1, electrosurgical system 100 is illustrated, which includes a single generator 102, an electrosurgical instrument 104, and a return electrode 106. Generator 102, in a preferred embodiment, is an RF wave generator that produces RF electrical energy and communicates the RF electrical energy to electrosurgical instrument 104 via cable 108. Electrosurgical instrument 104 includes a hand piece or pencil 110 and an electrode tip 112. Electrosurgical instrument 104 communicates the RF electrical energy to a patient to cut tissue and/or cauterize blood vessels of the patient's body. Specifically, an electrical discharge is delivered from tip 112 to the patient in order to cause the heating of cellular matter of the patient that is in extremely close contact to tip 112. The heating takes place at an appropriately high temperature to allow electrosurgical instrument 104 to be used to perform electrosurgery. Return electrode 106 and cable 114 provide a return electrical path to wave generator 102 for any excess charge that dissipated into surrounding tissue of the patient's body.

Figure 2:
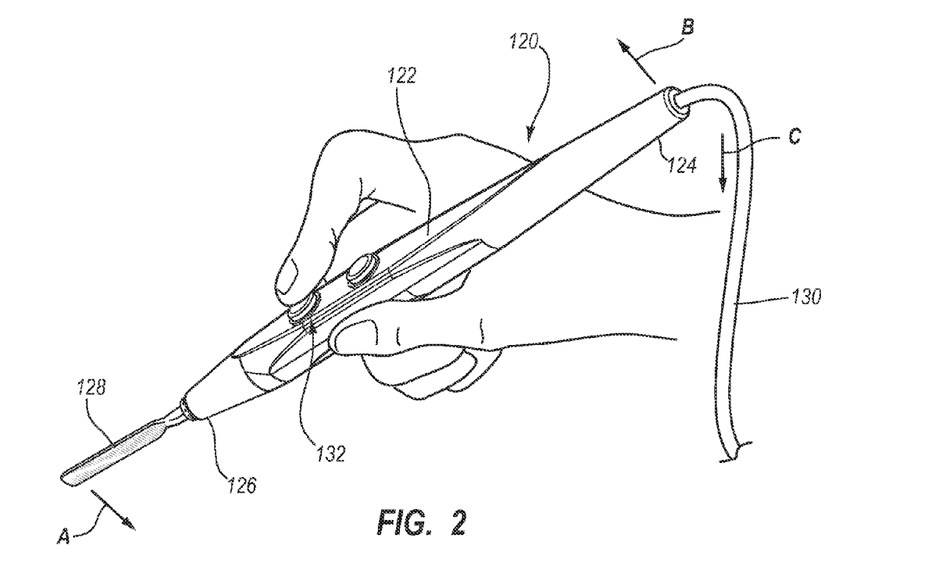
FIG. 2 illustrates one manner of holding an electrosurgical instrument.

Illustrated in FIG. 2 is an electrosurgical instrument 120 commonly used to perform electrosurgical procedures. Electrosurgical instrument 120 includes a hand piece 122 having a proximal end 124 and a distal end 126. An electrode tip 128 is received within distal end 126. A cable 130 is connected to electrosurgical instrument 120 at proximal end 124. Cable 130 communicates electrical energy from an electrosurgical generator, such as generator 102 in FIG. 1, to electrosurgical instrument 120. The electrical energy is passed through electrode tip 128 and into a patient's tissue.

Electrosurgical instruments, such as electrosurgical instrument 120, are commonly referred to as electrosurgical pencils or pens because in use they are generally often held in the same manner as a pencil or pen when writing. FIG. 2 illustrates the most common manner in which physicians hold electrosurgical instrument 120 during an electrosurgical procedure. As can be seen, hand piece 122 is laid through the crook of the hand and is held in place by the middle finger and thumb. The index finger is placed on top of hand piece 122 to further hold hand piece 122 in place as well as to activate input device 132.

As noted elsewhere herein, the flexibility, weight/moment-arm and drag characteristics of cable 130 and the connection location of cable 130 to the hand piece 122 limit the ability of the physician during a surgical procedure. While holding electrosurgical instrument 120 as shown in FIG. 2, a physician will perform electrosurgery by activating input device 132 and moving electrode tip 128 into contact with the patient's tissue. To make contact between electrode tip 128 and the patient's tissue, the physician will move his or her wrist or fingers to adjust the position and/or orientation of electrosurgical instrument 120.

For instance, the physician may move his or her wrist so that electrode tip 128 moves in the direction of arrow A toward the patient's tissue. Notably, as the physician moves electrode tip 128 in the direction of arrow A, proximal end 124 moves in the direction of arrow B. The weight of cable 130 constantly pulls proximal end 124 in the direction of arrow C. Thus, the weight of cable 130 resists the movement of proximal end 124 in the direction of arrow B.

The resistance created by the weight of cable 130 is accentuated by the location at which cable 130 is connected to hand piece 122. As is understood, a torque is created by applying a force at a distance from an axis or pivot point. The magnitude of the torque is a result of the magnitude of the applied force and the distance between the axis/pivot point and the location where the force is applied. In the case of electrosurgical instrument 120, the weight of cable 130 is the force that contributes to the generation of the resistive torque. Additionally, the location at which cable 130 attaches to hand piece 122 and how hand piece 122 is held creates the lever arm through which the weight of cable 130 works to create the torque. More specifically, cable 130 enters hand piece 122 at or near proximal end 124. When electrosurgical instrument 120 is held as shown in FIG. 2, proximal end 124 is positioned above and away from the crook of the physician's hand, which acts as the pivot point. The weight of cable 130 pulls down on proximal end 124, thereby creating a torque or moment-arm. Because the magnitude of the torque is dependent on the distance between the pivot point and the force, the further apart the connection point between cable 130 and hand piece 122 is away from the crook of the hand, the greater the torque will be. The larger this torque is, the greater amount of resistance the physician will experience when manipulating electrosurgical instrument 120.

To overcome the resistance created by the weight of cable 130, the physician must exert additional energy to move electrosurgical instrument 120 into the desired orientation. Continuously working against the resistance created by cable 130 can cause the physician's hand, and/or wrist, and/or arm to become fatigued during an electrosurgical procedure. This fatigue can also lead to a loss of accuracy and precision in the performance of the procedure.

Attention is now directed to FIGS. 3-8, which illustrate embodiments of electrosurgical instruments which reduce the resistance created by the electrical cable that connects the electrosurgical instruments to an electrosurgical generator. The embodiments shown in FIGS. 3-8 include a connection point between the electrical cable and the hand piece that is more centrally located between the proximal and distal ends of the hand piece. Additionally, the hand pieces can include one or more grooves into which the cable can be received. The grooves and/or cable can be configured to allow a physician to select the point at which the cable will extend from the hand piece, referred to hereinafter as the "exit location" of the cable. By allowing the physician to select and adjust the exit location, the physician is able to reduce or eliminate the resistance created by the weight of the cable, which can reduce the fatigue experienced during an electrosurgical procedure.

Figure 3:
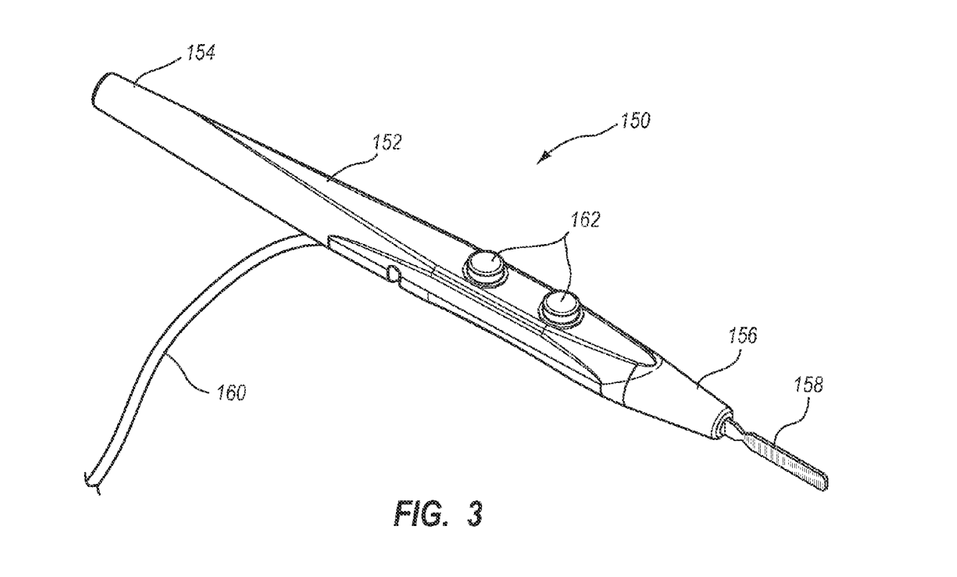
FIG. 3 is a perspective view of an electrosurgical instrument according to an exemplary embodiment of the present invention.
Figure 4:
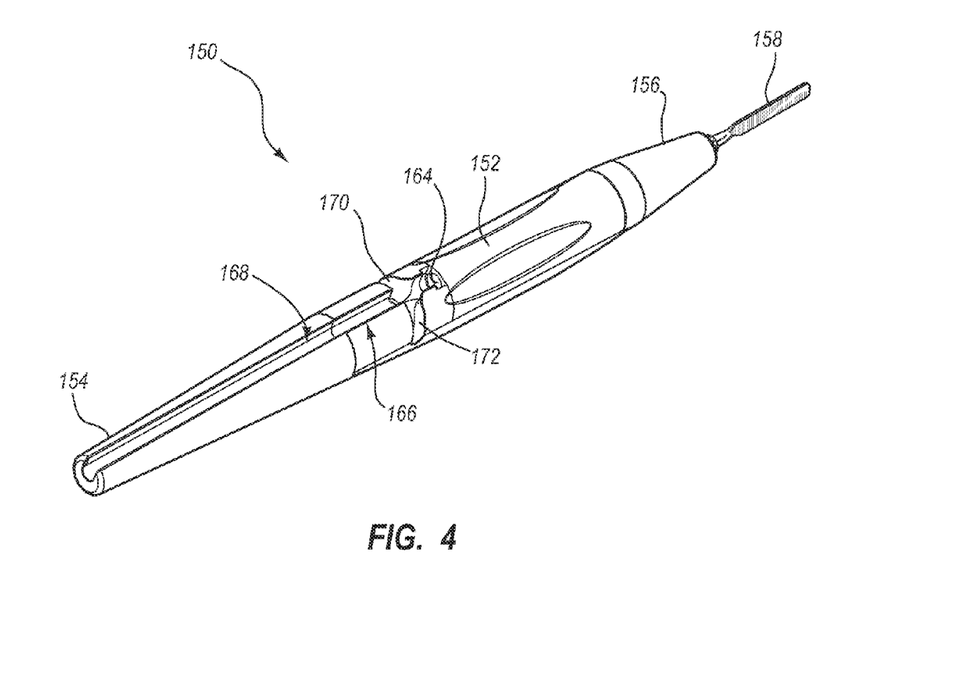
FIG. 4 is a bottom perspective view of the electrosurgical instrument of FIG. 3 showing a channel system formed in a hand piece of the electrosurgical instrument.
Figure 5:
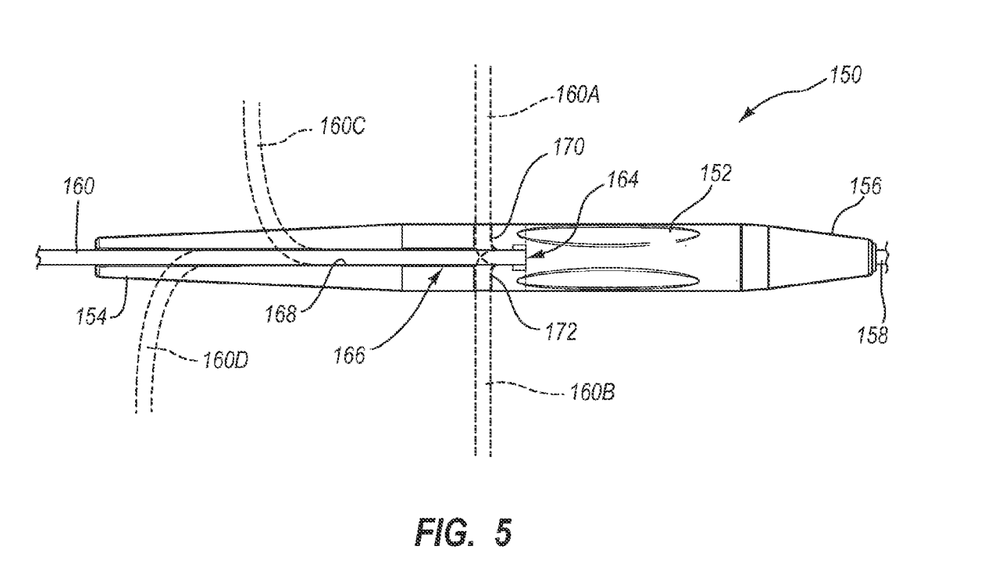
FIG. 5 is a bottom view of the electrosurgical instrument of FIG. 3 showing exemplary exit locations for an electrical cable that is connected to the hand piece of the electrosurgical instrument.

For example, FIGS. 3-5 illustrate one exemplary embodiment of an electrosurgical instrument 150 according to the present invention. Electrosurgical instrument 150 includes a hand piece 152 having a proximal end 154 and a distal end 156. Distal end 156 is configured to receive an electrode tip 158. Hand piece 152 is connected to cable 160, which delivers electrical energy from a generator, such as generator 102 in FIG. 1, to electrode tip 158. Hand piece 152 also includes input devices 162 for controlling the flow of electrical energy to electrode tip 158. As can be seen in FIG. 3, cable 160 extends from a central portion of hand piece 152 as opposed to extending from the proximal end of the hand piece as cable 130 does in FIG. 2.

FIG. 4 illustrates a bottom perspective view of electrosurgical instrument 150. As seen therein, hand piece 152 includes a receptacle 164. An end of cable 160 (not shown in FIG. 4) is inserted into receptacle 164 and connected to the internal components of hand piece 152 to provide electrical energy to electrode tip 158. Hand piece 152 also includes a channel system 166 that allows a physician to select the exit location of cable 160. In other words, while cable 160 is connected to hand piece 152 at receptacle 164, a portion of cable 160 can be positioned within channel system 166 so that cable 160 exits or extends from hand piece 152 at any one of a number of locations on hand piece 152, whether adjacent to or distant from receptacle 164.

In the exemplary embodiment illustrated in FIG. 4, channel system 166 includes a longitudinal channel 168 and opposing side channels 170 and 172. Each of channels 168, 170, and 172 begins near and extends away from receptacle 164. Longitudinal channel 168 generally extends in a straight line from receptacle 164 to proximal end 154. Opposing side channels 170 and 172 extend from receptacle 164 and out opposing sides of hand piece 152. Channels 168, 170, and 172 are each sized to selectively receive and retain at least a portion of cable 160 therein.

FIG. 5 depicts cable 160 exiting or extending away from hand piece 152 at various possible locations. For the sake of clarity, cable 160 is identified in FIG. 5 with reference numbers 160, 160A, 160B, 160C, and 160D. While references numbers 160, 160A, 160B, 160C, and 160D identify the same cable 160, the reference letters A, B, C, and D are used to aid in the following description of cable 160 exiting or extending from hand piece 152 at different locations. Similar lettering is also used elsewhere herein with reference to cables 192, 210, and 222.

As shown in FIG. 5, cable 160A can extend out of receptacle 164 and be positioned in channel 170 so that cable 160A extends out of the right side of hand piece 152 (when viewed from the top of hand piece 152). As noted above channel 170 can be sized to snuggly retain cable 160A therein so that cable 160A does not inadvertently come out of channel 170 while electrosurgical instrument 150 is being used.

Positioning cable 160A in channel 170 so that cable 160A exits hand piece 152 on the right side may be particularly comfortable for a left-handed physician. When cable 160A is positioned within channel 170, a left-handed physician may hold hand piece 152 so that cable 160A extends out of the right side of hand piece 152 towards the physician's thumb. The physician may allow cable 160A to extend in a downward direction below the thumb. Alternatively, the physician may position cable 160A so that it extends over the top of the thumb before extending in a downward direction.

Similarly, cable 160B can extend out of receptacle 164 and be positioned in channel 172 so that cable 160B extends out of the left side of hand piece 152 (when viewed from the top of hand piece 152). As with channel 170, channel 172 can be sized to snuggly retain cable 160B therein so that cable 160B does not inadvertently come out of channel 172 while electrosurgical instrument 150 is being used. Positioning cable 160B in channel 172 so that cable 160B exits hand piece 152 on the left side may be particularly comfortable for a right-handed physician. A right-handed physician holding hand piece 152 with cable 160B positioned within channel 172 can allow cable 160B to extend below or over the top of the thumb in the same manner as described above with reference to cable 160A and channel 170.

Positioning cable 160A/160B within channel 170/172, as shown in FIG. 5, significantly reduces or eliminates the resistance typically created by the electrical cable, as described above with reference to FIG. 2. When cable 160A/160B is positioned within channel 170/172, the exit location of cable 160A/160B is relatively close to the crook of the physician's hand. This positioning of the exit location for cable 160A/160B reduces the torque created by the cable. Specifically, because the distance between the applied force (i.e., the weight of the cable) and the pivot point (i.e., the crook of the hand) is relatively small, the torque created by cable 160A/160B is much smaller than the torque created by cable 130 described above with reference to FIG. 2. Due to the smaller torque, a physician will experience less resistance and fatigue when using electrosurgical instrument 150 with cable 160A/160B positioned within channel 170/172 as compared to a typical electrosurgical instrument in which the cable is connected at the proximal end.

Some physicians may prefer to have cable 160 exit hand piece 152 at a location other than those provided by channels 170 and 172. In such a case, the physician may use channel 168 to achieve a comfortable exit location for cable 160. To achieve the comfortable exit location, a physician may position a portion of cable 160 within channel 168 so that cable 160 extends from receptacle 164, through channel 168, and exits channel 168 at a desired location between receptacle 164 and proximal end 154.

For instance, with reference to cable 160C of FIG. 5, the physician may position an inch of cable 160C within channel 168 and then allow the remainder of cable 160C to remain free from hand piece 152. In such a case, cable 160C may exit hand piece 152 so that cable 160C lies in the crook of the hand and then falls in a downward direction near the physician's wrist. Alternatively, with reference to cable 160D of FIG. 5, the physician may position two inches of cable 160D within channel 168 and then allow the remainder of cable 160D to remain free from hand piece 152. In yet other situations, the physician may position cable 160 through the entire length of channel 168 so that cable 160 does not exit hand piece 152 until proximal end 154.

While five exit locations have been illustrated in FIG. 5, one associated with each of cables 160, 160A, 160B, 160C, and 160D, it will be readily understood that channel system 166 can provide still other exit locations for an electrical cable. Channel system 166 is configured to allow a physician to select any location along the length of channel 168 as an exit location. For instance, a physician with a larger hand may desire cable 160 to exit closer to proximal end 154. This can be accomplished by simply positioning more of cable 160 within channel 168 so that the exit location of cable 160 is closer to proximal end 154. Alternatively, a physician with a smaller hand may desire cable 160 to exit very near receptacle 164. This can be accomplished using channels 170 and 172 or by positioning only a short length of cable 160 within channel 168. Thus, channel system 166 allows a physician to customize hand piece 152 so that hand piece 152 is most comfortable to that physician and reduces the resistance and fatigue caused by cable 160.

Figure 6:
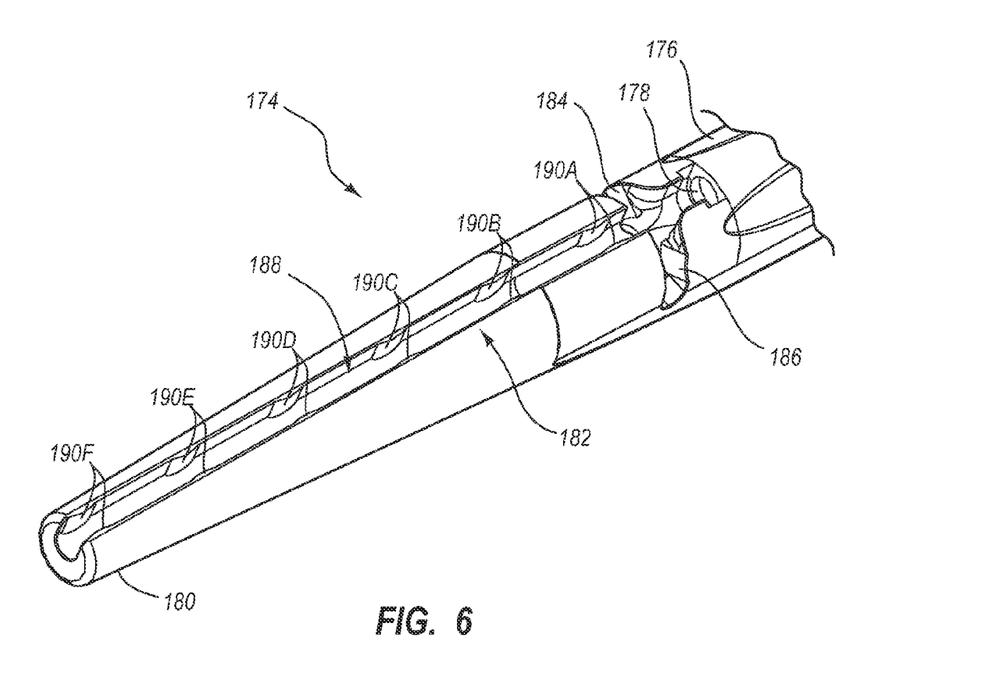
FIG. 6 is a bottom perspective view of a another exemplary embodiment of an electrosurgical instrument having a channel system according to the present invention.
Figure 7:
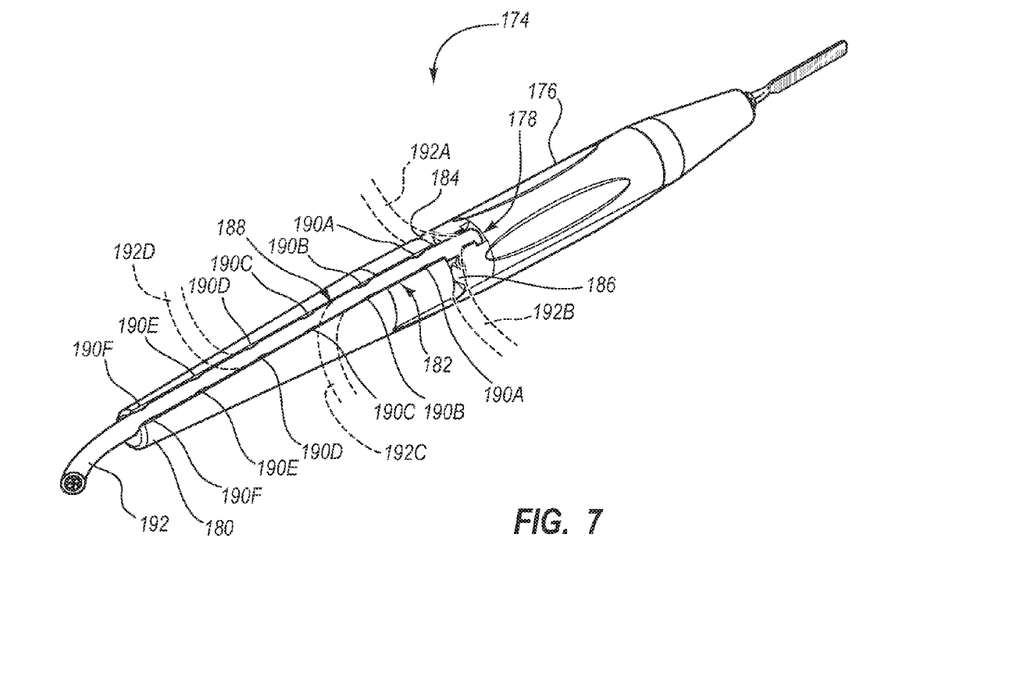
FIG. 7 is a bottom perspective view of the electrosurgical instrument of FIG. 6 showing exemplary exit locations for an electrical cable that is connected to the hand piece of the electrosurgical instrument.

Turning attention now to FIGS. 6 and 7, there is illustrated an alternative embodiment of a channel system that can be incorporated into an electrosurgical instrument. With specific reference to FIG. 6, there is shown an electrosurgical instrument 174 that includes a hand piece 176. Hand piece 176 includes a receptacle 178. An end of cable 192 (FIG. 7) is inserted into receptacle 178 and connected to the internal components of hand piece 176 to provide electrical energy to an electrode tip.

Hand piece 176 also includes a channel system 182 similar to channel system 166. Specifically, channel system 182 includes opposing side channels 184 and 186 and a longitudinal channel 188. Opposing side channels 184 and 186 are generally the same as channels 170 and 172 described above. Channel 188 is also similar to channel 168. Channel system 182 allows a physician to select the exit location of cable 192 in much the same manner as described above with reference to channel system 166. More particularly, a physician may select the exit location of cable 192 by positioning cable 192 within one of channels 184, 186, 188. Selection of channels 184 and 186 causes cable 192 to exit the sides of hand piece 176, similar to cable 160 exiting the sides of hand piece 152 through channels 170 and 172. In the case of using channel 188, the physician can also select from a number of pre-defined exit locations along the length of channel 188. Thus, channel system 182 allows a physician to customize electrosurgical instrument 174 so as to reduce the resistance and fatigue caused by cable 192 and make electrosurgical instrument 174 more comfortable to use.

While channel 188 is similar to channel 168, channel 188 further includes detents 190A, 190B, 190C, 190D, 190E, and 190F, collectively referred to as detents 190. Each of detents 190A, 190B, 190C, 190D, 190E, and 190F includes two opposing ridges positioned within channel 188. Detents 190 are configured to selectively receive and retain cable 192 therebetween. Thus, a physician may position cable 192 within channel 188 and between one or more of detents 190A, 190B, 190C, 190D, 190E, and 190F so as to hold cable 192 while the physician uses electrosurgical instrument 174.

Channel 168, described above, allows a physician to select an exit location anywhere along the length of channel 168. In contrast, detents 190 create a plurality of discrete exit locations for cable 192 along the length of channel 188. In other words, detents 190 provide a physician with the option of selecting an exit location from multiple, predefined exit locations.

As noted, detents 190 are configured to selectively retain cable 192 therebetween. The areas of channel 188 between detents 190 can be configured to allow cable 192 to exit channel 188 when subsequent detents 190A, 190B, 190C, 190D, 190E, and/or 190F are not employed to retain cable 192 within channel 188. For example, as illustrated in FIG. 7, a physician may position cable 192C within channel 188 so that cable 192C extends between detents 190A and 190B, but not between detents 190C, 190D, 190E, and 190F. In such a case, cable 192C is then able to exit channel 188 between detents 190B and 190C. Thus, the area between detents 190B and 190C constitutes one of the plurality of discrete exit locations for cable 190. Similarly, the physician may position cable 192D within channel 188 so that cable 192D extends between detents 190A, 190B, 190C, and 190D, but not between detents 190E and 190F. In such a case, cable 192D is then able to exit channel 188 between detents 190D and 190E. Thus, the area between detents 190D and 190E constitutes another one of the plurality of discrete exit locations for cable 190. The areas between detents 190A and 190B, 190C and 190D, and 190E and 190F can similarly constitute discrete exit location for cable 190. While channel 188 is illustrated in FIGS. 6 and 7 with six detents 190 and five exit locations, it will be understood that a channel system can be formed with fewer or more than six detents 190 and five exit locations.

Channel system 182 therefore provides a physician with the ability to customize electrosurgical instrument 174 in order to reduce the resistance and fatigue caused by cable 192. Additionally, channel system 182 also allows the physician to adjust the exit location of cable 192 to make electrosurgical instrument 174 more comfortable for the physician.

Figure 8:
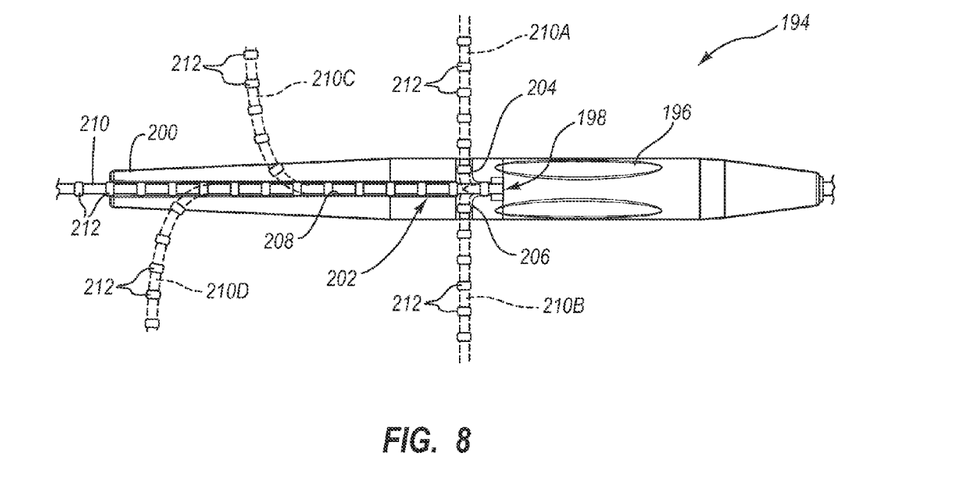
FIG. 8 is a bottom perspective view of yet another exemplary embodiment of an electrosurgical instrument having a channel system according to the present invention.

FIG. 8 illustrates yet another embodiment of an electrosurgical instrument 194 that reduces the resistance and fatigue caused by the weight and connection location of a cable to the hand piece. In the illustrated embodiment, electrosurgical instrument 194 includes a hand piece 196 having a receptacle 198, a proximal end 200, and a channel system 202. As with receptacles 164 and 178, receptacle 198 is configured to receive an end of cable 210, which provides electrical energy to an electrode tip. Channel system 202 is generally the same as channel system 166. In particular, channel system 202 includes opposing side channels 204 and 206 and a longitudinal channel 208, each of which is sized and configured to selectively receive and retain cable 210 therein.

As with the previous channel systems described herein, channel system 202 allows a physician to select the exit location of cable 210, thereby making electrosurgical instrument 194 more comfortable and reducing the resistance created by the cable. In the present embodiment, however, cable 210 includes a plurality of detents 212 on its outer surface and along its length. Detents 212 provide similar functionality as detents 190 described above. In particular, detents 212 can be sized to snuggly fit within channels 204, 206, and 208 so that cable 210 is retained therein. In addition, detents 212 can be used to select how much of cable 210 is retained within channel system 202. For instance, a physician may position cable 210C within channel 208 so that six detents 212 are held within channel 208, and the remainder of cable 210C is able to hang freely out of channel 208. Alternatively, the physician may position more detents 212 of cable 210 within channel 208, as shown with cable 210D, so that the exit location of cable 210 is closer to proximal end 200. In this manner, the physician may again select from a plurality of predefined, discrete exit location for cable 210, similar to the predefined, discrete exit locations discussed with reference to FIGS. 6 and 7. In this case, however, the predefined, discrete exit locations are created by detents 212 on cable 210 rather than detents 190 formed in the channel system.

Figure 9:
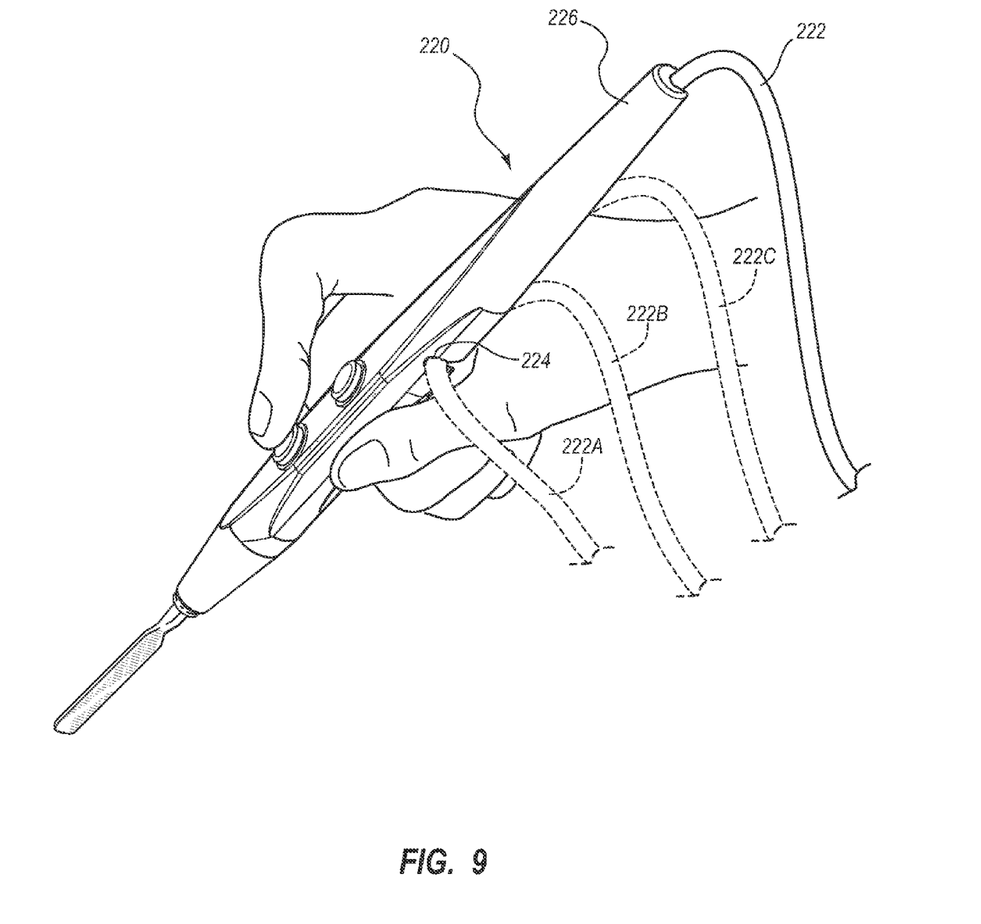
FIG. 9 illustrates an electrosurgical instrument according to the present invention being held with the electrical cable exiting the electrosurgical instrument from multiple exemplary exit locations.

FIG. 9 illustrates an electrosurgical instrument 220. Electrosurgical instrument 220 can incorporate any one of the channel systems and/or cables/hoses 222 described herein. FIG. 9 illustrates a few examples of where and how a cable or hose 222 exits the electrosurgical instrument 220 and falls relative to a physician's hand. For instance, cable 222A exits electrosurgical instrument 220 through a side channel 224. As can be seen, cable 222A extends out of electrosurgical instrument 220 toward the physician's thumb. Alternatively, the physician can have cable 222B exit electrosurgical instrument 220 near the crook of the hand so that cable 222B extends down the crook of the hand towards the wrist. The physician may further select an exit location for cable 222C that is closer to proximal end 226. Still further, the physician may elect to have cable 222 exit electrosurgical instrument 220 at proximal end 226, similar to a standard electrosurgical instrument.

A channel system according to the present invention may also be configured to accommodate multiple cables and/or hoses commonly associated with electrosurgical instruments. For instance, in addition to an electrical cable, many electrosurgical instruments include an evacuation hose to remove smoke from a surgical site during an electrosurgical procedure. As with the electrical cables, the evacuation hoses are commonly connected to the proximal end of the hand piece, thereby creating resistance to the movement of the electrosurgical instrument. This resistance can, like the resistance from the electrical cables, cause the physician to experience fatigue during an electrosurgical procedure.

To reduce the fatigue caused by the evacuation hoses, a channel system as described here can be incorporated in the electrosurgical instrument to allow the physician to adjust the exit location of the evacuation hose. For instance, a channel system can be incorporated that allows the evacuation hose to exit the hand piece at a location closer to the physician's hand, thereby reducing the torque created by the weight of the evacuation hose. As described above, the channel system can be configured to allow the physician to select the exit location from anywhere along the length of the hand piece, or from one of a plurality of predefined, discrete exit locations.

It is understood that the features of the above described embodiments are not exclusive to one another. Rather, one of ordinary skill in the art will recognize that the described features can be combined and/or modified as may be needed or desired. For example, the channels of the various channel systems can have generally smooth interior surfaces or they can be formed with detents, either of which can receive a cable/hose with a generally smooth outer surface. Alternatively, the channels, whether with smooth surfaces or detents, can receive a cable/hose that has detents of its own formed thereon.

Furthermore, while each of the channel systems have been shown and described as having two opposing side channels and a single longitudinal channel, it will be understood that a channel system according to the present invention can be formed with a single side channel, a single longitudinal channel, multiple side channels, multiple longitudinal channels, or a combination thereof For instance, a channel system may include one or more side channels along the length of the hand piece, each of which exits to the same side of the hand piece. A channel system may also have multiple side channels on each side of the hand piece. Furthermore, a channel system may have multiple channels, some sized for an electrical cable and some sized for an evacuation hose. Still further, a channel system may have one or more channels that are configured to receive and selectively retain an electrical cable and an evacuation hose in the same channel at the same time.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An electrosurgical instrument for use during an electrosurgical procedure to transmit electrical energy from an electrosurgical generator to tissue of a patient, the electrosurgical instrument comprising a hand piece that is receptive to a conductive electrode tip, and an electrical cable configured to transmit the electrical energy from the electrosurgical generator to the hand piece, the hand piece comprising:
   a proximal end and a distal end, the distal end being configured to receive a conductive electrode tip at least partially therein;
   a receptacle disposed between the proximal end and the distal end and configured to receive therein an end of the electrical cable;
   an input device configured to selectively control the transmission of the electrical energy to the tissue of a patient; and
   a channel system configured to receive and retain therein at least a portion of the electrical cable, wherein the channel system enables an exit location of the electrical cable from the channel system to be selectively adjusted such that the exit location may be selectively moved along a length of the hand piece between the receptacle and the proximal end.

2. The electrosurgical instrument of claim 1, wherein the channel system comprises a longitudinal channel extending from the receptacle to the proximal end of the hand piece.

3. The electrosurgical instrument of claim 2, wherein the longitudinal channel comprises a plurality of detents spaced along a longitudinal length of the longitudinal channel, the plurality of detents being configured to selectively retain at least a portion of the electrical cable within the longitudinal channel.

4. The electrosurgical instrument of claim 3, wherein the longitudinal channel further defines a plurality of predefined, discrete exit locations from which the electrical cable can exit the longitudinal channel.

5. The electrosurgical instrument of claim 4, wherein the plurality of predefined, discrete exit locations are formed along the longitudinal length of the longitudinal channel and between the plurality of detents.

6. The electrosurgical instrument of claim 5, wherein the channel system is configured to enable the user of the electrosurgical instrument to adjust the electrical cable to select an exit location from the plurality of predefined, discrete exit locations from which the electrical cable may exit the channel system.

7. The electrosurgical instrument of claim 1, wherein the channel system comprises one or more channels that enable the user to selectively adjust an exit location of an evacuation hose that is connected to the hand piece.

8. The electrosurgical instrument of claim 1, wherein the channel system comprises:
   a longitudinal channel that extends from the receptacle toward the proximal end and along at least a portion of the length of the hand piece, wherein the longitudinal channel is configured to selectively receive at least a portion of the electrical cable therein; and
   a side channel that extends from the receptacle to one side of the hand piece, wherein the side channel is configured to selectively receive at least a portion of the electrical cable therein, and wherein the user of the electrosurgical instrument can selectively position the electrical cable within the longitudinal channel or the side channel.

9. An electrosurgical instrument for use during an electrosurgical procedure to transmit electrical energy from an electrosurgical generator to tissue of a patient, the electrosurgical instrument comprising:
   an electrical cable configured to transmit the electrical energy from the electrosurgical generator; and
   a hand piece having a proximal end, a distal end, and a central portion disposed therebetween, the distal end being configured to receive a conductive electrode tip at least partially therein, the central portion having a receptacle configured to receive therein an end of the electrical cable, the hand piece further comprising a channel system configured to receive and retain therein at least a portion of the electrical cable, wherein the channel system enables a user of the electrosurgical instrument to select an exit location for the electrical cable from a plurality of exit locations, wherein the channel system comprises:
      a side channel that extends from the receptacle to one side of the hand piece and is configured to selectively and removably receive at least a portion of the electrical cable therein such that the electrical cable exits the channel system from the central portion of the hand piece; and
      a longitudinal channel that extends from the receptacle toward the proximal end, wherein the longitudinal channel is configured to selectively and removably receive at least a portion of the electrical cable therein such that the electrical cable exits the channel system between the receptacle and the proximal end, and wherein the user of the electrosurgical instrument can selectively position the electrical cable within the longitudinal channel or the side channel to select the exit location of the electrical cable from the channel system.

10. The electrosurgical instrument of claim 9, further comprising a second side channel that extends from the receptacle to a second side of the hand piece and is configured to selectively and removably receive at least a portion of the electrical cable therein such that the electrical cable exits the channel system from the central portion and on the second side of the hand piece.

11. The electrosurgical instrument of claim 10, wherein the side channel and the second side channel respectively define first and second exit locations of the plurality of exit locations.

12. The electrosurgical instrument of claim 9, wherein the side channel defines a first exit location of the plurality of exit locations and the longitudinal channel defines at least two exit locations of the plurality of exit locations.

13. The electrosurgical instrument of claim 12, wherein the at least two exit locations defined by the longitudinal channel are located between detents formed in the longitudinal channel.

14. The electrosurgical instrument of claim 9, wherein the user is able to select any location along the length of the longitudinal channel as an exit location.

15. The electrosurgical instrument of claim 9, wherein electrical cable is formed with a plurality of detents on an outer surface thereof.

16. The electrosurgical instrument of claim 15, wherein the locations of the plurality of exit locations are determined by the spacing between the plurality of detents on the electrical cable and the number of detents received within the channel system.

17. An electrosurgical instrument for use during an electrosurgical procedure to transmit electrical energy from an electrosurgical generator to tissue of a patient, the electrosurgical instrument comprising:

an electrical cable coupleable to the electrosurgical generator and configured to transmit the electrical energy from the electrosurgical generator;

a hand piece having a proximal end, a distal end, and a central portion disposed therebetween, the central portion having a receptacle configured to receive therein an end of the electrical cable, the hand piece further comprising a channel system that enables a user of the electrosurgical instrument to selectively position at least a portion of the electrical cable within the channel system to thereby select an exit location from the channel system for the electrical cable, wherein the channel system comprises:

first and second opposing side channels that extend from the receptacle to opposing sides of the hand piece, the first and second opposing side channels being configured to selectively and removably receive at least a portion of the electrical cable therein such that the electrical cable may exit the channel system from the central portion on either side of the hand piece; and a longitudinal channel that extends from the receptacle toward the proximal end, wherein the longitudinal channel comprises a plurality of detents spaced along a length of the longitudinal channel, the plurality of detents being configured to selectively and removably receive at least a portion of the electrical cable therebetween, wherein the plurality of detents defines a plurality of discrete exit locations from which the electrical cable can exit the channel system, wherein the user of the electrosurgical instrument can selectively position the electrical cable within the first side channel, the second side channel, or the longitudinal channel to select the exit location of the electrical cable from the channel system; and a conductive electrode tip configured to be received within the distal end of the hand piece and transmit the electrical energy to the tissue of a patient.

18. The electrosurgical instrument of claim 17, wherein the hand piece comprises one or more additional side channels through which the electrical cable can exit the channel system.

19. The electrosurgical instrument of claim 17, wherein the channel system comprises one or more channels that enable the user to selectively adjust an exit location of an evacuation hose that is connected to the hand piece.

20. The electrosurgical instrument of claim 19, wherein the channel system is configured to allow the evacuation hose to exit the channel system from the central portion of the hand piece.

* * * * *